US009119622B2

(12) United States Patent
Rahmani

(10) Patent No.: US 9,119,622 B2
(45) Date of Patent: Sep. 1, 2015

(54) METHODS AND APPARATUSES FOR RESHAPING THE ESOPHAGUS AND OTHER BODY LUMENS

(75) Inventor: Emad Y. Rahmani, Indianapolis, IN (US)

(73) Assignee: Indiana University Research & Technology Corporation, Indianapolis, IN (US)

( * ) Notice: Subject to any disclaimer, the term of this patent is extended or adjusted under 35 U.S.C. 154(b) by 0 days.

(21) Appl. No.: 12/721,894

(22) Filed: Mar. 11, 2010

(65) Prior Publication Data

US 2010/0168512 A1 Jul. 1, 2010

Related U.S. Application Data

(60) Division of application No. 11/762,431, filed on Jun. 13, 2007, now Pat. No. 7,727,249, which is a continuation of application No. PCT/US2007/068149, filed on May 3, 2007.

(60) Provisional application No. 60/797,346, filed on May 3, 2006.

(51) Int. Cl.
*A61B 1/00* (2006.01)
*A61B 17/10* (2006.01)
*A61B 17/12* (2006.01)
(Continued)

(52) U.S. Cl.
CPC ......... *A61B 17/12013* (2013.01); *A61B 1/2736* (2013.01); *A61B 17/32056* (2013.01); *A61B 2017/00269* (2013.01); *A61B 2017/00827* (2013.01); *A61B 2017/12018* (2013.01); *A61B 2017/306* (2013.01); *A61B 2018/00577* (2013.01); *A61B 2018/00595* (2013.01); *A61B 2018/141* (2013.01); *A61B 2018/1407* (2013.01)

(58) Field of Classification Search
CPC ............... A61B 17/12013; A61B 17/32056; A61B 2017/12018; A61B 17/00269; A61B 17/00827; A61B 1/2736; A61B 17/12009
USPC ................. 606/139, 140, 144, 148, 151, 157
See application file for complete search history.

(56) References Cited

U.S. PATENT DOCUMENTS 3,870,048 A * 3/1975 Yoon .............................. 606/141
3,967,625 A * 7/1976 Yoon .............................. 128/831
(Continued)

FOREIGN PATENT DOCUMENTS

DE 29824314 12/2000
EP 1547531 6/2005
(Continued)

OTHER PUBLICATIONS

International Search Report, PCT/US07/68149, 4 pages.
(Continued)

*Primary Examiner* — Julian W Woo
*Assistant Examiner* — Shaun L David
(74) *Attorney, Agent, or Firm* — Woodard, Emhardt, Moriarty, McNett & Henry LLP

(57) ABSTRACT

Described are methods and systems for treating a patient to modify a body passage of the patient. The methods may involve removing tissue from a luminal surface of a body passage such as the esophagus or stomach, for the purpose of inducing a healing response that will result in a reshaping of the body passage.

22 Claims, 11 Drawing Sheets

(51) Int. Cl.
*A61B 1/273* (2006.01)
*A61B 17/3205* (2006.01)
*A61B 17/00* (2006.01)
*A61B 17/30* (2006.01)
*A61B 18/00* (2006.01)
*A61B 18/14* (2006.01)

(56) References Cited

U.S. PATENT DOCUMENTS

| | | | | |
|---|---|---|---|---|
| 4,226,239 A * | 10/1980 | Polk et al. | | 606/141 |
| 4,471,766 A * | 9/1984 | Terayama | | 600/104 |
| 4,493,320 A | 1/1985 | Treat | | |
| 5,141,515 A * | 8/1992 | Eberbach | | 606/151 |
| 5,224,497 A | 7/1993 | Ehlers | | |
| 5,234,445 A * | 8/1993 | Walker et al. | | 606/148 |
| 5,269,789 A * | 12/1993 | Chin et al. | | 606/140 |
| 5,290,284 A * | 3/1994 | Adair | | 606/37 |
| 5,320,630 A * | 6/1994 | Ahmed | | 606/140 |
| 5,398,844 A * | 3/1995 | Zaslavsky et al. | | 221/208 |
| 5,403,326 A | 4/1995 | Harrison et al. | | |
| 5,462,559 A * | 10/1995 | Ahmed | | 606/140 |
| 5,507,797 A * | 4/1996 | Suzuki et al. | | 606/140 |
| 5,624,453 A * | 4/1997 | Ahmed | | 606/140 |
| 5,693,059 A * | 12/1997 | Yoon | | 606/139 |
| 5,741,273 A * | 4/1998 | O'Regan | | 606/140 |
| 5,853,416 A * | 12/1998 | Tolkoff | | 606/140 |
| 5,897,487 A * | 4/1999 | Ouchi | | 600/127 |
| 5,913,865 A * | 6/1999 | Fortier et al. | | 606/140 |
| 5,947,983 A | 9/1999 | Solar et al. | | |
| 6,007,551 A | 12/1999 | Peifer et al. | | |
| RE36,629 E * | 3/2000 | Zaslavsky et al. | | 221/208 |
| 6,042,591 A * | 3/2000 | Mears | | 606/140 |
| 6,059,719 A | 5/2000 | Yamamoto | | |
| 6,059,797 A * | 5/2000 | Mears | | 606/140 |
| 6,280,452 B1 * | 8/2001 | Mears | | 606/140 |
| 6,436,108 B1 * | 8/2002 | Mears | | 606/140 |
| 6,632,227 B2 | 10/2003 | Adams | | |
| 6,663,639 B1 * | 12/2003 | Laufer et al. | | 606/139 |
| 6,676,672 B2 * | 1/2004 | Chu et al. | | 606/139 |
| 6,676,674 B1 * | 1/2004 | Dudai | | 606/151 |
| 6,685,713 B1 * | 2/2004 | Ahmed | | 606/140 |
| 6,730,101 B1 | 5/2004 | Peifer et al. | | |
| 6,773,440 B2 | 8/2004 | Gannoe | | |
| 6,835,199 B2 * | 12/2004 | McGuckin et al. | | 606/142 |
| 6,974,466 B2 | 12/2005 | Ahmed et al. | | |
| 7,037,344 B2 * | 5/2006 | Kagan et al. | | 623/23.65 |
| 2003/0225312 A1 | 12/2003 | Suzuki et al. | | |
| 2004/0082963 A1 * | 4/2004 | Gannoe et al. | | 606/153 |
| 2005/0033115 A1 | 2/2005 | Okada | | |
| 2005/0055038 A1 | 3/2005 | Kelleher et al. | | |
| 2006/0206063 A1 | 9/2006 | Kagan et al. | | |
| 2007/0167676 A1 | 7/2007 | Miyamoto et al. | | |

FOREIGN PATENT DOCUMENTS

| | | |
|---|---|---|
| JP | 2000-139933 | 5/2000 |
| JP | 2001 275993 A | 10/2001 |
| JP | 2005-058343 | 3/2005 |
| WO | WO 95/01305 | 12/1995 |
| WO | WO 2005/112797 | 12/2005 |

OTHER PUBLICATIONS

Seltman et al., "Endoscopic Measurement of Cardia Circumference as an Indicator of GERD," Gastrointestinal Endoscopy, vol. 63, No. 1 (2006) pp. 22-31.
Written Opinion, PCT/US07/68149, pages.
Machine Translation dated Sep. 12, 2014 of JP 2005058343A, dated Mar. 10, 2005—Hood for Endoscope and Demucosation Implement for Endoscope.
Machine Translation dated Sep. 12, 2014 of JP2000139933A, dated May 23, 2000—Treatment Tool for Endoscope.

\* cited by examiner

METHODS AND APPARATUSES FOR RESHAPING THE ESOPHAGUS AND OTHER BODY LUMENS

REFERENCE TO RELATED APPLICATION

The present application is a divisional of U.S. patent application Ser. No. 11/762,431, filed Jun. 13, 2007, issued as U.S. Pat. No. 7,727,249, which is a continuation of PCT Patent Application Serial No. PCT/US07/68149 filed May 3, 2007, entitled "METHODS AND APPARATUSES FOR RESHAPING THE ESOPHAGUS AND OTHER BODY LUMENS" and which claims the benefit of U.S. Provisional Patent Application Ser. No. 60/797,346 filed May 3, 2006 entitled "METHODS AND APPARATUSES FOR RESHAPING THE ESOPHAGUS AND OTHER BODY LUMENS" all of which are hereby incorporated by reference in their entirety.

BACKGROUND

The present invention relates generally to the field of medicine and in particular aspects to methods and apparatuses for reshaping the esophagus or other body lumens.

Gastroesophageal reflux disease (GERD) has been described as an improper functioning of the lower or inferior esophageal sphincter (LES) in which stomach contents are able to leak back, or reflux, abnormally into the esophagus. When refluxed stomach acid contacts the lining of the esophagus, it causes a burning sensation in the chest or throat called heartburn. Reports show that as many as 10 percent of Americans have daily episodes of heartburn and that up to 44 percent have symptoms at least once a month. While occasional heartburn is common and does not necessarily mean that the subject has GERD, chronic heartburn may signify GERD and can lead to more serious health problems.

Esophagitis, a complication of GERD, can become a relapsing chronic condition. Other complications of GERD include strictures, ulcerations and Barrett's esophagus (progressive replacement of distal eroded squamous mucosa with metaplastic intestinal epithelium). Treatment of GERD may include medication and/or surgery.

Morbid obesity (clinically severe obesity) has been described as a condition in which a person's weight creates major primary or threatened secondary effects on the patient's health and well being. Unfortunately, morbid obesity often results in early death. A 12-year follow-up of 336,442 men and 419,060 women found that the mortality rate increased approximately two-fold for men having a 50% above-average weight, while the mortality rate increased 5-fold for diabetics and 4-fold for those with digestive tract disease in this same group. In a similar group of women, the overall mortality rate also increased two-fold, while the mortality rate increased 8-fold for diabetics and 3-fold for those with digestive tract disease.

Associations between the average weight of population groups and the prevalence of non-insulin-dependent diabetes have also been repeatedly observed. Reports show that the risk of developing diabetes increases about two-fold in the mildly obese, five-fold in the moderately obese and ten-fold in severely obese persons. It is also known that the duration of obesity is an important determinant of the risk for developing diabetes. Further, studies show increases in cancer mortality rates in severely obese females, e.g., endometrium (5.4 times), gall bladder (3.6 times), uterine cervix (2.4 times), ovary (1.6 times) and breast (1.5 times). As well, studies show increases in cancer mortality rates in severely obese males, e.g., colorectal (1.7 times) and prostate (1.3 times).

There remains a need for improved and/or alternative methods and apparatuses that are useful for treating GERD, obesity and other medical conditions. The present invention is addressed to those needs.

SUMMARY

In one aspect of the invention, methods for treating a patient are provided that include reshaping a body lumen or passageway of the patient by a procedure including selective tissue removal which, upon healing, results in the reshaping. In particular embodiments, the invention provides methods that comprise an endoluminal mucosaplasty (ELM) procedure in which tissue from a wall defining the body passageway is removed to invoke a healing process that reshapes the passageway, and systems designed therefor. The resected tissue can be non-diseased tissue. In certain inventive procedures, these methods may be used to modify an esophagus to a new condition that provides increased resistance to reflux of gastric contents, for instance in the treatment of a patient having gastrointestinal reflux disease (GERD). In other inventive procedures, these methods can be used to modify the stomach in a bariatric surgery to contribute to a change in eating habits of the patient, e.g. in the treatment of obesity. In certain forms, the inventive methods lead to a narrowing of a body passageway. Such methods may include the steps of (i) identifying a body passageway within a patient presenting a medical condition in which a reduction in the luminal diameter of the body passageway will reduce flow therethrough in at least one direction such that the patient will experience at least a partial relief of the medical condition; (ii) determining a degree of reduction in the diameter of the passageway expected to provide effective treatment for the medical condition in the patient; (iii) removing tissue from an inner portion of a wall defining the body passageway sufficient to elicit a healing response. The ensuing healing of the tissue can cause contraction of tissues within the body passageway such that the luminal diameter thereof is reduced. In many typical treatment regimens, the patient will then be assessed postoperatively to determine if the body passageway reduction is effective for at least partial relief of the medical condition.

In one embodiment, the present invention provides a method for treating a patient comprising resecting tissue from a luminal surface of a body passage of the patient for the purpose of inducing a healing response that will result in a reshaping of the body passage.

In another embodiment, the invention provides a system for reshaping a body lumen. The system comprises an endoscope configured to generate an image of the body lumen and at least one reference of known dimension located in the body lumen, and software for calculating a dimension of the body lumen based on a comparison of the reference and the body lumen in the image. The system further includes an endoluminal surgical device for removing tissue from the body lumen.

In another embodiment, the invention provides a medical device comprising an endoscopic ligator barrel, one or more ligation bands received upon the ligation barrel, and a single pull line operably associated with said one or more ligation bands, said single pull line operable to deploy said one or more ligation bands from said ligation barrel. The device can also include an endoscope upon which the barrel is received.

In another embodiment, the invention provides a medical device comprising an endoscopic ligator barrel having a proximal end and a beveled distal end, and one or more ligation bands received upon the ligation barrel, said one or more ligation bands being deployable from said beveled distal end. The device can further include an endoscope upon which the barrel is received.

In another embodiment, the present invention provides a method for narrowing a body passageway, comprising (a) identifying a body passageway within a patient presenting with a known medical condition in which the effective reduction in the nominal luminal diameter of said body passageway will lessen flow therethrough in at least one direction such that said patient will experience at least partial relief of said medical condition; (b) determining a degree of reduction in the diameter of said passageway expected to provide effective treatment for said medical condition in said patient; (c) using a medical device to cause injury to a portion of the luminal surface of said body passage sufficient to elicit a healing response that causes contraction of the tissues within said body passageway such that the nominal luminal diameter thereof is reduced without causing injury to the muscular layer of said body passageway; and (d) assessing said patient post-operatively to determine if said body passageway reduction is effective for at least partial relief of said medical condition.

In another embodiment, the present invention provides a method for treating a patient that comprises reshaping the gastroesophageal junction of the patient with an endoscopic procedure that includes removing non-diseased tissue, wherein said reshaping is effective to reduce gastroesophageal reflux in the patient.

In another embodiment, the invention provides a method for treating a patient comprising reshaping the stomach of the patient with an endoscopic procedure that includes removing non-diseased tissue, wherein said reshaping creates a narrowing in the stomach to modify satiety sensation of the patient.

In other embodiments, the invention provides method for treating a patient comprising operating through a channel of an endoscope to remove patient tissue (i) for the purpose of modifying the esophagus of the patient to reduce reflux of gastric contents into the esophagus; or (ii) for the purpose of modifying the cardia of the patient to treat obesity.

In another embodiment, the present invention provides a method for treating a patient comprising responding to an identified need in the patient for treatment to reduce gastroesophageal reflux or obesity by conducting an endoscopic procedure that includes removing tissue of the patient's esophagus and/or cardia.

In another embodiment, the invention provides a method for treating a patient comprising (a) diagnosing a patient as having GERD; and (b) based on said diagnosing, conducting an endoscopic procedure that includes removing patient tissue for the purpose of modifying the shape of the gastroesophageal junction of the patient.

In another embodiment, the present invention provides a method for treating a patient comprising (a) diagnosing a patient as needing treatment for obesity; and (b) based on said diagnosing, conducting an endoscopic procedure that includes removing patient tissue for the purpose of modifying the shape of the cardia of the patient.

In another embodiment, the invention provides a method for narrowing a body passageway comprising the steps of (a) endoscopically visualizing a portion of said body passageway selected for modification to provide a reduced luminal diameter thereof; (b) determining the degree of reduction required to provide the reduced luminal diameter; (c) identifying a first treatment site located on a luminal surface of the body passageway; (d) capturing a first portion of tissue at the first treatment site; (e) placing a tissue-securing element around the captured first portion of tissue; (f) excising the first captured portion of tissue; (g) identifying a second treatment site located circumferentially adjacent to said first site; (h) capturing a second portion of tissue at the second treatment site; (i) placing a tissue-securing element around the captured second portion of tissue; and (j) excising the second captured portion of tissue.

In another embodiment, the invention provides a method for narrowing a body passageway that is at least partially dysfunctional with respect to restriction of materials flowing therethrough, comprising the steps of (a) selecting a first zone of treatment extending along a length of said body passageway, said first zone of treatment extending circumferentially around the inner surface of said body passageway; (b) establishing a nominal diameter of the body passageway within the zone of treatment; (c) calculating an amount of resected tissue effective to reduce the body passageway to a desired second nominal diameter smaller than said first nominal diameter such that said dysfunctional condition is at least partially corrected; (d) visualizing the zone of treatment using an imaging device; (e) isolating a first portion of the mucosa and submucosa from muscle layer within said first zone of treatment; (f) resecting the first portion of the mucosa and submucosa above said muscle layer using a medical device; (g) moving circumferentially of said body passageway adjacent the first resected portion of tissue to a second portion of tissue spaced apart from said first portion; and (h) resecting said second portion of tissue leaving an untreated area of tissue between said first portion and said second portion of resected tissue.

In another embodiment, the invention provides a method for narrowing a body passageway comprising excising luminal tissue of the body passageway to create a resected area in a configuration that promotes healing of the luminal tissue such that there is an overall contraction of the luminal tissue during the healing process whereby the nominal luminal diameter of the body passageway is reduced.

In another embodiment, the present invention provides a method for treating a patient to modify a body passage of the patient, comprising removing tissue from a luminal surface of the body passage without substantial damage to underlying muscle tissue of the passage for the purpose of inducing a healing response that will result in a reshaping of the body passage.

In further embodiments, the present invention provides kits for reshaping a body passage such as an esophagus or stomach, as described herein, that include means or devices as described herein for resecting or otherwise removing tissue from the lumen of the body passage, and written materials regarding use of the means or devices to reshape a body passage, e.g. in the treatment of GERD or obesity as described herein.

Additional embodiments as well as features and advantages of the invention will be apparent from the further descriptions herein.

DETAILED DESCRIPTION

Figure 1A:
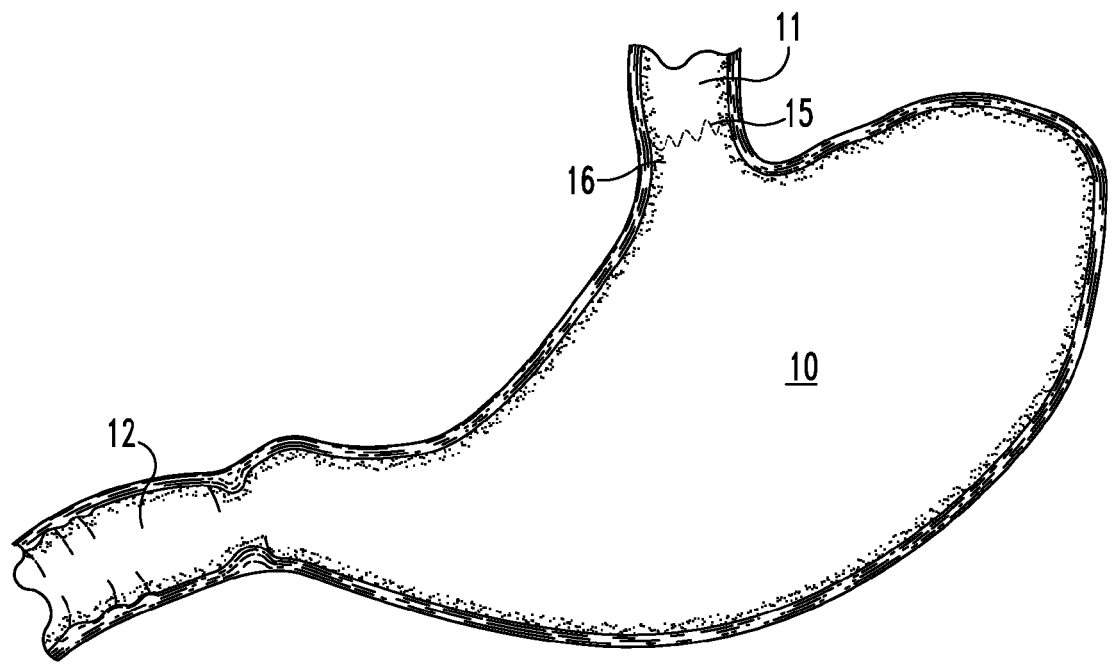
FIG. 1A is a schematic drawing of the stomach in cross-section.

For the purposes of promoting an understanding of the principles of the disclosure, reference will now be made to the embodiment illustrated in the drawings and specific language will be used to describe the same. It will nevertheless be understood that no limitation of the scope of the claims is thereby intended, such alterations and further modifications in the illustrated device, and such further applications of the principles of the disclosure as illustrated therein, being contemplated as would normally occur to one skilled in the art to which the disclosure relates.

As disclosed above, aspects of the present invention relate to methods and systems for reshaping body lumens such as those of the esophagus or stomach. This reshaping may, for example, be effective to modify the flow of materials within the body lumen. Such reshaping can involve decreasing the resting diameter of the body lumen, creating folds or irregular surfaces within a body lumen wall, and/or altering the contour of the inner periphery of a body lumen wall. These and other modifications that can affect the flow of materials within the lumen are contemplated as being a part of the present invention.

As noted above, in particular inventive aspects, methods and systems are provided for reshaping a region of an esophagus of a patient, especially a region at or near the gastroesophageal junction. Such procedures can be undertaken, for example, to result in a reduction of gastroesophageal reflux potentially in the treatment of a patient diagnosed with GERD. In addition or alternatively, procedures to reduce reflux can involve the treatment and reshaping of non-esophageal tissues as well, for example cardia tissues occurring just below the termination of the esophagus.

GERD is typically diagnosed or at least suspected when a person complains of heartburn. Heartburn is frequently described as a sub-sternal (under the middle of the chest) burning that occurs after meals and often worsens when lying down. When suspected, the treating physician will often conduct a therapeutic trial (at least initially) in which the patient is treated with medications to suppress the production of acid by the stomach. The diagnosis is then confirmed on the basis of a response of the symptoms to the treatment. For example, if the heartburn is diminished to a large extent by the medication, the diagnosis of GERD is generally considered confirmed. GERD can be diagnosed in a number of other suitable manners as well, for example, using diagnostic and other tests including but not limited to endoscopic procedures and esophageal acid testing. Oftentimes, the abnormal reflux associated with GERD is due to the presence of a patient gastroesophageal junction that is distended or over-sized (e.g., has a diameter that is considered too large). In inventive variants, such an over-sized gastroesophageal junction is subjected to a reshaping treatment in order to reduce its diameter and thereby reduce the amount of gastric reflux into the esophagus.

In additional embodiments of the invention, methods and systems are provided for modifying the lumen of the stomach of a patient, for example, in a bariatric surgery potentially in the treatment for obesity. Such procedures can, for example, be undertaken to treat patients that have been diagnosed as being morbidly obese. Typically, morbid obesity is diagnosed when a person's weight creates major primary or threatened secondary effects on the patient's health and well being. The usual diagnostic threshold for this condition is 100 pounds over what is considered ideal body weight, e.g., as determined by standard height versus weight charts. Examples of obesity-aggravated secondary health problems are arthritic symptoms on weight-bearing joints, adult-onset diabetes, sleep apnea/severe snoring, hygiene problems related to skin folds, depression and low self-esteem. In accordance with one aspect of the invention, a stricture or other narrowing or reshaping can be created in the stomach lumen of a patient who is morbidly obese or another patient for which modification of eating habits is considered to be beneficial. The stricture or other reshaping modifies the passage of food materials through the stomach lumen so as to facilitate a modification of eating habits in the patient. In addition, as all or a portion of the procedure, tissue from the fundus of the stomach can be removed, so as to reshape (e.g. reduce the size of) the stomach and potentially result in the removal of cells, such as ghrelin-secreting epithelial cells, that secrete hormonal or other signals related to hunger. Ghrelin is understood to be a hormonal signal for hunger, and the reduction or removal of cells that secrete ghrelin or other hunger signals may be used in inventive embodiments disclosed herein, e.g. for the treatment of obesity.

Endoluminal mucosaplasty procedures can be used in the inventive reshaping methods disclosed herein. In this regard, "endoluminal mucosaplasty" as used herein refers to an endoluminally conducted procedure which results in a change in the mucosa tissue that lines the body lumen under treatment. This change may, for example, be a change in the diameter of the presented mucosal surface of the passageway, in the presence or absence of folds or ridges, and the like.

Some inventive reshaping methods described herein comprise resecting an amount of tissue from a body lumen wall and/or subjecting tissue at a treatment site to an injurious stimulus which results in cellular death within the tissue and an ensuing tissue healing response. In some forms of the invention, the tissue that is removed will include at least some non-diseased tissue for which there is no alternate indication (other than the desired reshaping) requiring its removal, and in certain instances all tissue that is removed will be normal non-diseased tissue for which there is no other indication for removal.

In advantageous inventive embodiments, the tissue that is removed will be essentially confined to tissue that occurs to the luminal side of a discernable muscular layer of the passageway wall. Lumen walls of body passageways such as the esophagus and stomach generally include a mucosal layer and an underlying submucosal connective tissue layer, commonly followed by a muscular layer. In aspects of the present invention, amounts of mucosa and/or submucosa are removed at a location without causing any substantial damage to the underlying muscle layer. In this regard, it is known that the connective tissue of submucosal layers often interleaves with amounts of muscle tissue, especially but not exclusively in areas transitioning from histologically-identifiable submucosa layers to underlying muscle layers. It will thus be understood that some muscular tissue can be present in the removed tissue without having caused any substantial damage to the underlying muscle layer.

In some forms of the invention, the removal of both mucosal and submucosal tissues is sufficient to expose the underlying muscle layer. To protect against significant damage to the muscle layer, amounts of mucosal and submucosal tissue can be drawn away from the underlying muscle layer, for example, using preferential suction into a chamber or using physical grasping devices such as forceps, after which the drawn tissue is resected or otherwise removed. Illustratively, as discussed elsewhere herein, endoscopic equipment and techniques, such as but not limited to those that have traditionally been used in endoscopic mucosal resection (EMR) procedures which remove unhealthy tissue, can be used to accomplish this type of tissue removal. Other endoscopic and non-endoscopic devices and techniques may be used as well. In both endoscopic and non-endoscopic procedures, fluid (e.g., saline) injections may optionally be used to separate mucosal and submucosal tissue from an underlying muscle layer prior to tissue removal. These and/or other devices, techniques or materials can be used in certain procedures of the invention to separate or isolate amounts of the tissue targeted for removal from tissue to remain, e.g. in order to protect or insulate the remaining tissue during removal of the targeted tissue. Such selective tissue removal and protection can facilitate a more controlled pattern of injury to result in the desired shape modification while reducing the risk of undesired tissue damage and any potential complications associated therewith.

Medical procedures of the invention will involve the removal of amounts of tissue in at least one site of a body lumen wall and more typically at multiple sites contemplated as useful to achieve the desired reshaping of the lumen. For instance, amounts of tissue can be removed from two to ten sites, and in certain treatments from two to eight sites. These sites may be discrete from one another, i.e., leaving amounts of undisturbed patient tissue in between the sites, or they can overlap one another so as to create a larger contiguous region of removed tissue. Where multiple targeted removal sites are employed, at least some of them and often all of them will be positioned circumferentially relative to one another, although sites that are longitudinally spaced from one another can also be used. The tissue removal sites will be selected so as to result in the desired reshaping of the body lumen when a subsequent tissue healing process occurs. Such tissue healing will result in a contraction of the body lumen in the healed region, leading to the desired reshaping. In certain desired treatments, the tissue removal site or sites will result in a decrease in diameter of the lumen relative to the diameter prior to the treatment. In this regard, any appropriate decrease in diameter can be used in the treatment of the patient, including for example diameter decreases of at least about 10 percent, and oftentimes at least about 10 percent up to about 50 percent, or at least about 25 percent up to about 50 percent. In certain cases, it is expected that percent diameter decreases in the range of about 30 percent to about 35 percent will be achieved in the patient treatment.

Medical procedures of the invention are desirably performed in conjunction with a careful assessment of the characteristics of the body passageway to be treated, such as but not limited to its size, shape, lumen diameter, and/or tissue and cellular makeup, prior to removal of amounts of tissue. In this manner, the amount and pattern of tissue removal can be correlated to a desired and expected reduction in diameter and/or other reshaping characteristic. This assessment can be conducted in a variety of fashions, and may involve the use of any number of suitable devices and techniques that prove useful in providing a desired lumen reshaping. For example, some inventive apparatuses may include a device that can directly or indirectly measure one or more lumen wall dimensions. In preferred aspects, systems especially adapted for performing inventive procedures as described herein include an overall apparatus having both an ability to measure the diameter of the body lumen and to undertake tissue removal in the body lumen, so as to ultimately achieve the desired reduction in diameter and/or other reshaping. For these purposes, a video endoscope system can include an imaging means for creating a viewable image of the body lumen, at least one scaling reference of known dimension, means for calculating the diameter of the body lumen based upon a reference to the scaling reference, and a device for removing amounts of tissue from a body lumen wall. In this manner, the body lumen can be viewed, a measurement of the diameter of the lumen at a point of interest can be taken, and the apparatus can then be used to remove amounts of tissue in a desired pattern to achieve beneficial reshaping of the lumen. It should be noted that such an imaging means may be useful in other regards, for example, in allowing the surgeon to view certain anatomical markers or other guidelines during an inventive procedure, which can help ensure that tissue removal occurs where desired.

A body lumen diameter can be calculated in a variety of fashions, and in some embodiments, is accomplished using software incorporated into the endoluminal operating system. Illustratively, inventive systems can incorporate software that is able to indirectly measure the diameter of a lumen at a location along the length of a body passageway, for example, by comparing software-based measurements, such as those based on vectors displayed on an imaging means, with a reference article of known diameter (e.g., an anatomical feature or mechanical article, such as a ligation barrel or another viewable portion of an endoscope). Then, this measurement can be used to determine an effective amount and pattern of tissue removal to achieve a desired result, such as but not limited to a desired reduction in the lumen diameter.

Reshaping procedures can include removal of tissue from a substantial percentage of the circumference of the inner surface of a body lumen wall at one or more desired locations along the length of the wall. For instance, removal of tissue from about 30% to 100% of such a circumference at a desired longitudinal location can be used, and in this regard, it will be understood that in inventive procedures involving tissue removal from the circumference of more than one longitudinal location along a body lumen wall, any suitable percentage of the body lumen wall circumference can be removed at each longitudinal location. For example, in an inventive procedure involving tissue removal from the circumference of a first region (e.g., above the lower esophageal sphincter) and a second region (e.g., below the lower esophageal sphincter), the percentage of tissue removed from the first region (in terms of the region's circumference) may be the same as or different from the percentage of tissue removed from the second region circumference. Illustratively, in some forms, the same general percentage of tissue is removed from the circumference of each of these regions, yet because the second region circumference is typically greater than the first region circumference, more actual tissue (in terms of circumference length) is removed from the second region circumference. In other forms, the percentage of tissue removed from the second region circumference will be about 10% to about 200% greater than the amount of actual tissue remove removed from the circumference of the first region, although other percentage differences are contemplated within the scope of the invention. It should be noted that in measuring the percentage of tissue removed from the circumference of the inner surface of a body lumen wall, such a measurement may be practically based on an average or nominal circumference length, for example, to account for folds, ridges, bumps or other surface irregularities in the body lumen wall inner surface.

For reshaping of the gastroesophageal junction to reduce reflux of gastric contents into the esophagus, certain inventive procedures will typically involve the removal of tissue from about 30% to about 70% of the circumference of the lumen wall at one or more locations in and/or around the junction. Illustratively, tissue can be removed directly at and/or near the junction, slightly above the junction and/or slightly below the junction, to achieve the desired result, e.g. a reduction in the diameter of the junction and/or a lengthening of the junction. For creating a stricture in the stomach, e.g., to modify the eating habits of the patient, about 60% to about 100% of the circumference of one or more regions of the stomach, especially the gastric cardia, will typically be subjected to tissue removal.

Tissue removal can also involve a significant longitudinal swath. For instance, longitudinal dimensions of the regions of tissue removal will typically be at least about 0.25 centimeters, and more typically in the range of about 0.5 centimeters to about 3 centimeters. In will be understood, however, that other longitudinal tissue removal lengths can be used within the broader aspects of the present invention.

Advantageously, the reshaping of a body lumen achieved in accordance with embodiments of the invention is largely or completely reversible, for instance, by dilating the treated region after it has partially or completely healed. Full or partial reversal may be desirable for a number of reasons, for example, where a patient has trouble swallowing or wants to resume pre-treatment eating habits. In some forms, the diameter of a gastroesophageal junction, which is determined to be too small after treatment and healing, can be dilated to a modified, enlarged diameter. Dilation of a body lumen segment can be accomplished in any suitable manner, e.g., using a balloon or other expandable device. Such an enlarged diameter may be the pre-treatment diameter, or a diameter between the pre-treatment diameter and the initial healed diameter. Similar principles apply to strictures created in the stomach.

Moreover, should the diameter or other reshaping of the body lumen after an initial tissue removal and healing phase be to an extent that is insufficient to result in the desired modified flow of material through the lumen, follow-up procedures similarly conducted to remove additional amounts of tissue can be undertaken to result in further reshaping.

A variety of devices and techniques can be used to achieve tissue removal according to the invention. Suitable such devices can be effective for resecting or otherwise removing tissues, especially essentially mucosal and submucosal tissues. In some embodiments, an inventive tissue removal apparatus is comprised of a tubular surgical access device equipped with (or otherwise usable in conjunction with) suitable direct or indirect (e.g. imaging) visualization means. Although not necessary to broader aspects of the invention, endoscopic devices and techniques, including those that have traditionally been used in endoscopic mucosal resection techniques are useful in some inventive embodiments. These include both non-ligated tissue capture/resection techniques, which may involve a preceding injection of saline or other fluid to lift the tissue to be removed from an underlying muscle layer, and ligated tissue capture/resection techniques and associated instrumentation therefor. In ligating techniques, a ligating barrel can be affixed to the end of an endoscope. Suction can be used to draw mucosal and submucosal tissues into the ligating barrel, and a ligating band thereafter deployed to result in a ligated tissue mass. An electrosurgical snare or other similar device can then be used to resect the ligated tissue. Desirably, the endoscopic apparatus will include an electrosurgical snare receivable through the operating channel of the endoscope and effective to resect the ligated tissue mass, although snares passed separately and/or outside of the endoscope may be employed as well. One suitable multiple-band ligating apparatus that can be used in methods of the invention is the Duette® Multi-Band Mucosectomy device commercially available from Wilson-Cook Medical, Inc., dba Cook™ Endoscopy, Winston-Salem, N.C., USA.

The Duette® device is the subject of an international patent application entitled "System and Method for Endoscopic Treatment of Tissue" (WO2005112797), published Dec. 1, 2005, and a United States provisional patent application entitled "System and Method for Endoscopic Treatment of Tissue" filed Mar. 31, 2006, each of which is hereby incorporated by reference in its entirety. The Duette® device kit includes a 7FR Soft AcuSnare™ Mini Hexagonal Head disposable polypectomy snare (Wilson-Cook Medical, Inc.). This snare has a soft hexagonal snare loop (size 1.5 cm×2.5 cm) made with braided stainless steel cable, and a catheter sheath size of 7.0 FR. The snare is connectable to an electrocautery unit and a modified multi-band ligator. The braided stainless steel cable provides a hexagonal operating loop (or snare head) with a combination of flexibility, strength and resiliency that permits multiple resections of tissue without breaking or excessively deforming. The multi-band ligator which is available with 4, 6, or 10 bands, has a relatively large operating channel bore so that the snare can be advanced through the working lumen of the endoscopy device to slice away tissue that has been captured by a deployed ligation band. Multiple ligations and resections can be conveniently accomplished with this device with no substantial deformation occurring to the snare.

Referring now to the drawings, illustrative, non-limiting systems and procedures of the invention will be described. FIG. 1A illustrates the stomach and adjacent portions of the anatomy including the esophagus 11 and the duodenum 12. The lower esophageal sphincter is generally indicated at 15. At least one of the goals of some inventive procedures is to reshape and narrow one or more portions of this body passageway such as, for example, between the esophagus 11 and the stomach 10. Illustratively, an inventive procedure may be used to treat GERD by narrowing the gastrointestinal junction to provide a more effective barrier against the reflux of acid and food contents from the stomach back into the esophagus. Still another procedure involves treating the cardia 16 below the gastrointestinal junction to narrow the passageway into the stomach so as to reduce an obese patient's food intake capacity for the purpose of contributing to weight loss. Although not necessary to broader aspects of the invention, in certain embodiments, such procedures include an endoluminal mucosaplasty procedure. Other suitable tissue removal and/or injury techniques, whether performed endoscopically or not, may be used in accordance with the invention to reshape or otherwise treat these or other body lumens. Other candidate body lumens include but not limited to the anal sphincter area which can be treated to remodel tissues of this area to improve compliance of the anal sphincter to treat fecal incontinence and/or other medical problems.

Figure 1B:
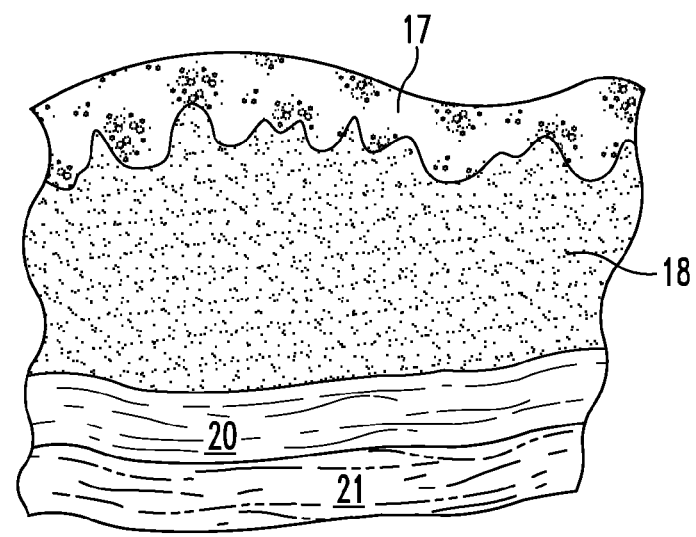
FIG. 1B is a cross-sectional view of the wall of the stomach and esophagus.
Figure 2:
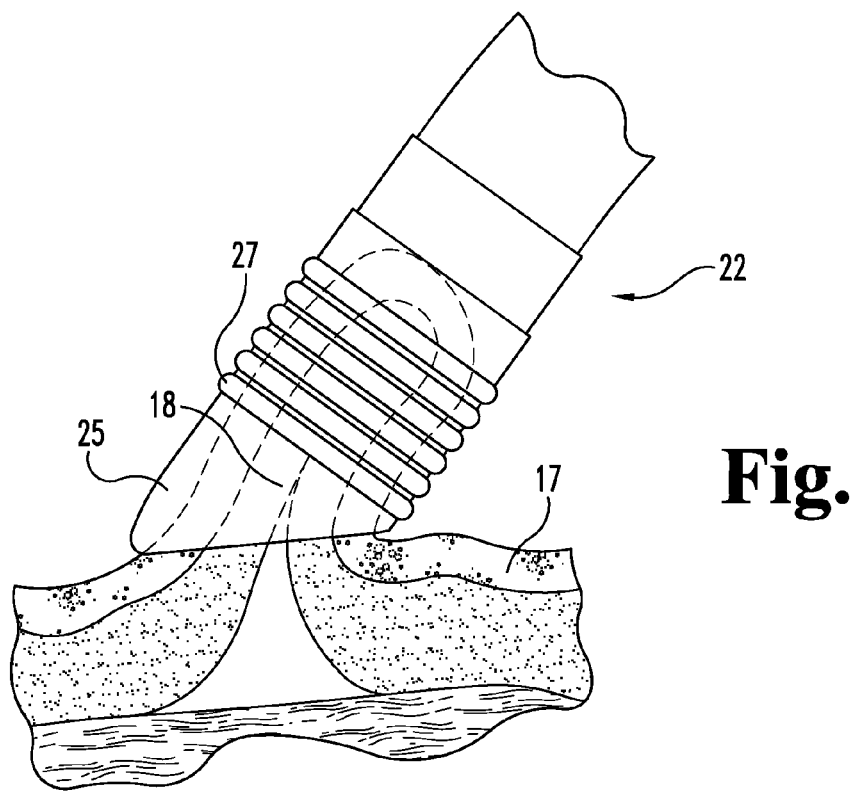
FIG. 2 is a view showing a step in an inventive process.
Figure 3:
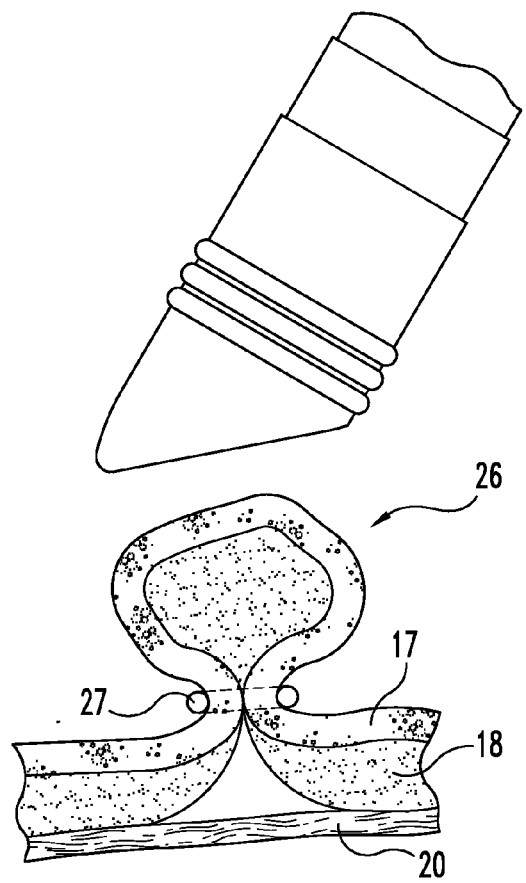
FIGS. 3-5 are views showing further steps in an inventive process.

Referring to FIG. 1B, there is illustrated a section of the wall between the esophagus and stomach and showing the mucosa layer 17, submucosa layer 18, muscle layer 20 and adventitia or serosa layer 21. Referring to FIG. 2, the multi-band ligator 22 is shown with a beveled barrel 25. Beveled barrels such as that shown in FIG. 2, disposed upon an endoscope, can facilitate the capture of tissue at preferred angles, although it will be understood that a variety of other beveled and non-beveled barrels may be utilized as well. Suction is provided in the beveled barrel 25 of the ligator, thereby causing tissue of the mucosa layer 17 and the submucosa layer 18 to pull away from muscle 20 and be drawn into the barrel 25. The multi-band ligator 22 is then operated to deploy an elastic band 27 from the barrel 25 onto the captured tissue 26 to produce the result shown in FIG. 3, wherein the elastic band 27 has the illustrated reduced size based upon its elasticity, capturing a mass of tissue. Although FIG. 2 shows multi-band ligator 22 having six elastic bands, it will be understood that this and other similar multi-band ligators useful in the invention can include any suitable number of elastic bands, and in some instances, will include one to ten or more elastic bands, more typically two to eight elastic bands. In the illustrated and preferred embodiment, the captured tissue 26 includes essentially only mucosa and submucosa and does not include any significant amount of captured muscle layer 20. After the tissue is captured with the band, the suction can be released or discontinued.

Figure 4:
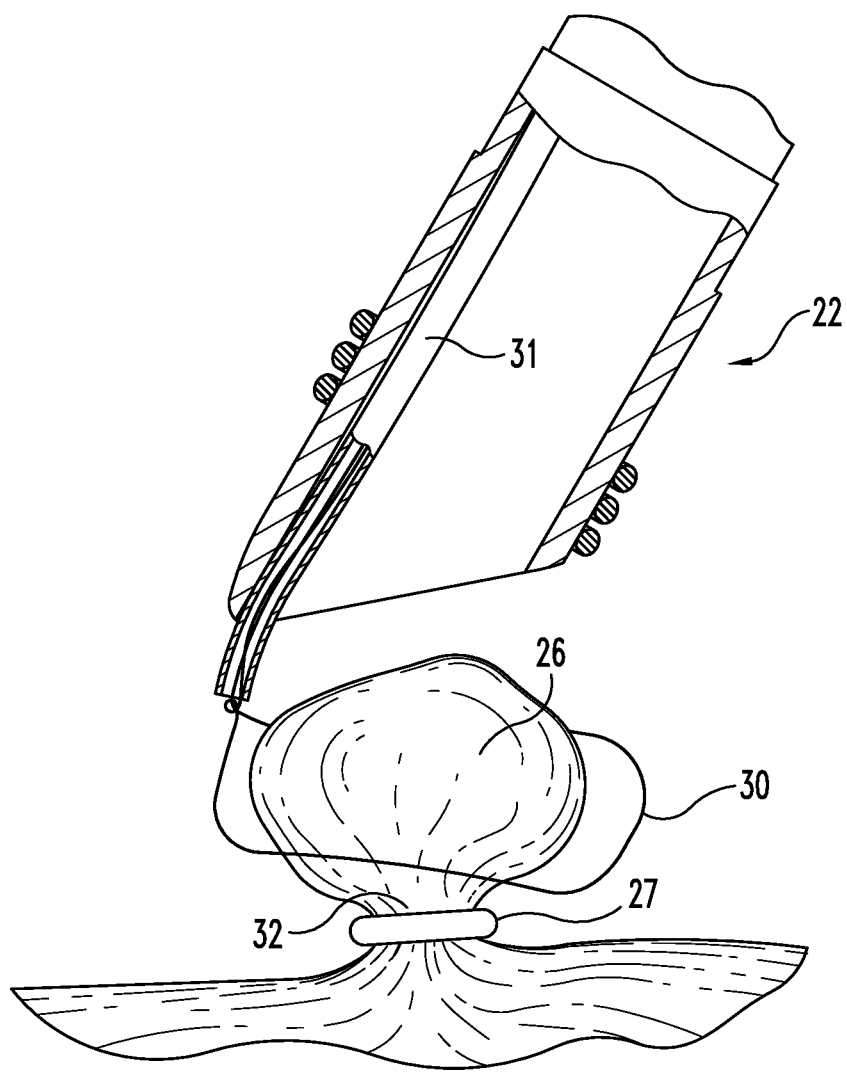
Figure 5:
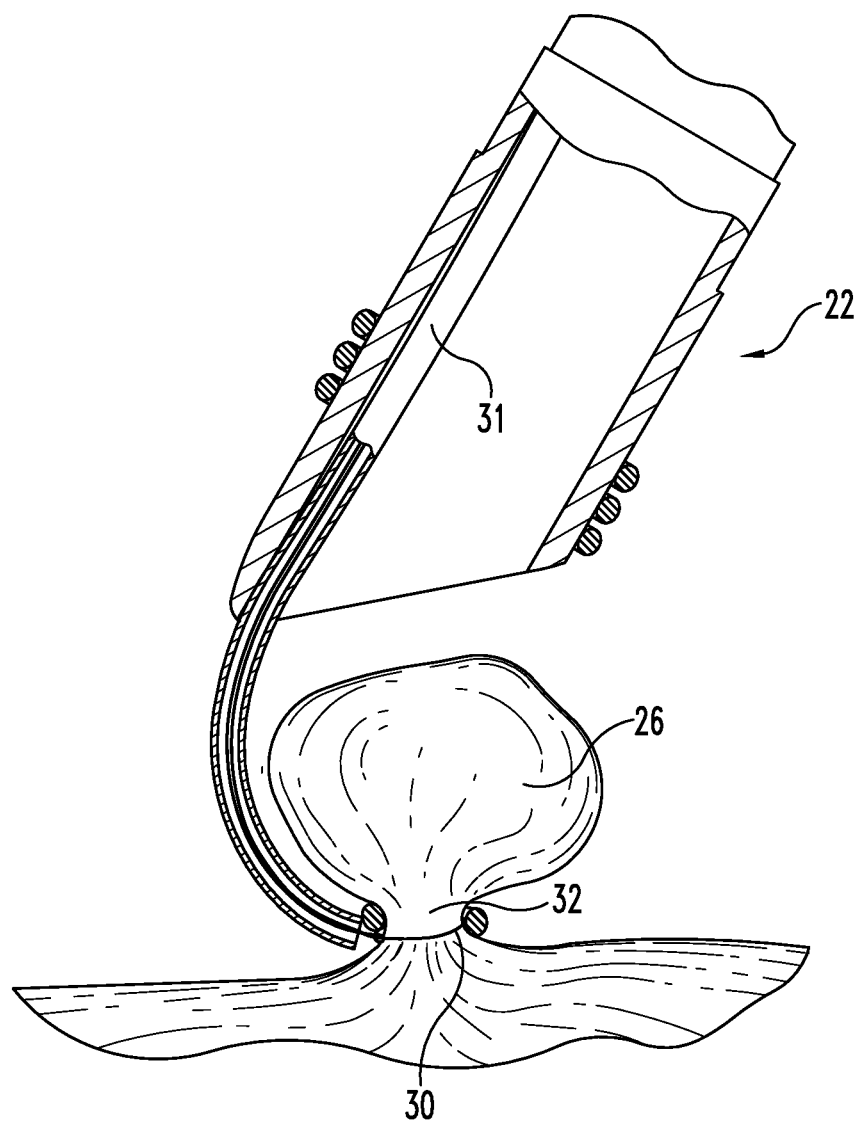
Figure 6:
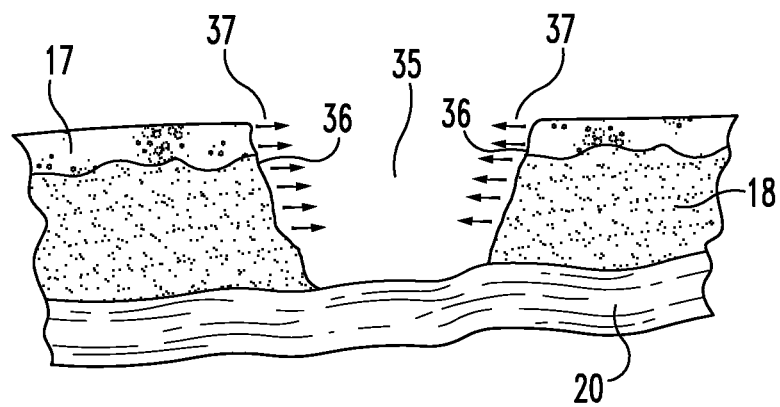
FIGS. 6-7 are sectional views of a body lumen wall showing healing response.

Referring to FIG. 4, the multi-band ligator 22 further includes a snare 30 which is connected to an electrocautery unit. The snare 30 is operated through a catheter 31 to tighten the snare 30 about the base 32 of the captured tissue 26 as generally shown in FIG. 5. The tightened snare can be positioned above or below the band 27, and in some modes, will occur around the band 27 or traversing the band 27 (i.e., with portions above and below the band 27). The snare 30 is then used to slice away and cauterize the tissue, causing the resulting resection edges 35 (FIG. 6) to extend down into the submucosa, exposing a portion of muscle layer 20 as shown. In doing so, an amount of muscular tissue may also be removed and/or some non-removed muscular tissue may be damaged at the site.

In some forms, the deep resection of cut 35 through the mucosa and submucosa and down to the muscle layer causes the healing of the cut area to occur primarily from the edges 36 of the wound as indicated by the arrows 37, more so than from the bottom of the wound as can occur, for example, in a typical ulceration of superficial cuts of the mucosa. Such healing causes the sides or edges 36 of the wound to move toward one another as new tissue is formed in and around the wound, which in turn, can be effective to pull tight tissues adjacent to sides 36, and in this regard, such generally lateral healing can be highly effective in reducing the passage diameter in regions in and/or around the inferior esophageal sphincter (e.g., in lower regions of the esophagus and/or upper regions of the cardia). Additionally, such healing in certain forms can cause a beneficial thickening of underlying muscle tissue in such regions.

Figure 7:
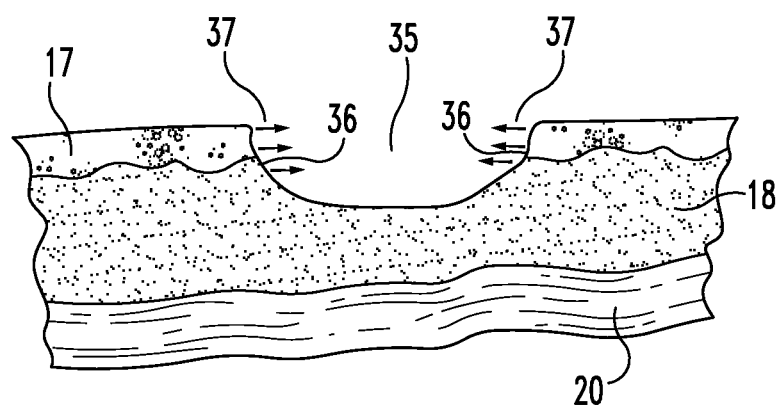

In general, the healing response initiated can depend on a number of factors including but not limited to the wounded tissue(s) involved, the devices and techniques used to remove and/or traumatize the tissue(s), and the size and shape of the wound(s) created. In this regard, it will be understood that wounds resulting from procedures of the invention can exhibit any suitable size, shape and configuration to achieve the desired reshaping. Illustratively, FIG. 7 shows an alternative cut 35, which extends at least partially down into the submucosa. The relatively deep extension of the cut 35 into the submucosa causes at least some of the healing of the cut area to generally occur from the sides 36 of the wound as indicated by the arrows 37.

Inventive methods may be used in treating patients who have GERD. For example, some methods involve reshaping the alimentary canal about the gastroesophageal junction so as to reduce the size of this junction such that the luminal opening has a final diameter (i.e., when healed) less than the original or pre-treatment diameter. In many adult humans, it will be desirable to reduce the diameter of the gastroesophageal junction, but not below approximately 15 mm to 18 mm when in a relaxed condition, although it will be understood that the appropriate diameter will vary from patient to patient within, above, or below this range.

In certain individuals, dimensions below this level will increase the likelihood of dysphagia (difficulty in swallowing). It will be understood, however, that these and other similar considerations will be undertaken by the health care provider, and re-sizing and final sizes or shapes of the body lumen will depend upon a variety of factors specific to the patient.

Figure 8:
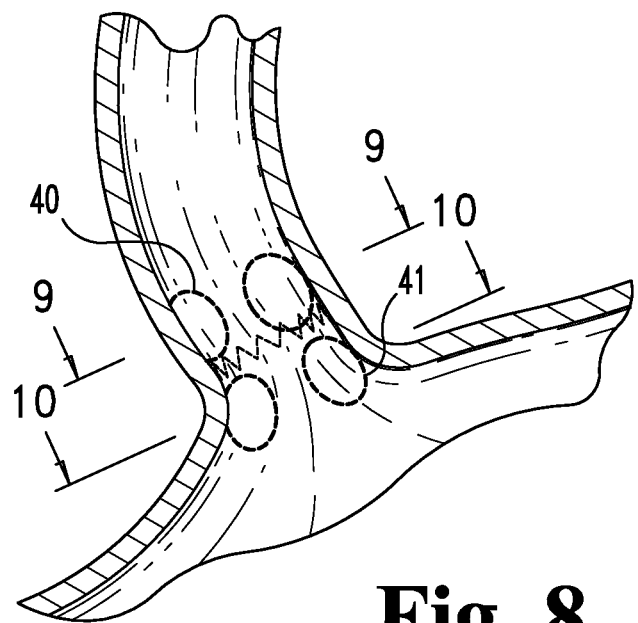
FIG. 8 is a sectional view of the junction of the stomach and the esophagus.
Figure 9:
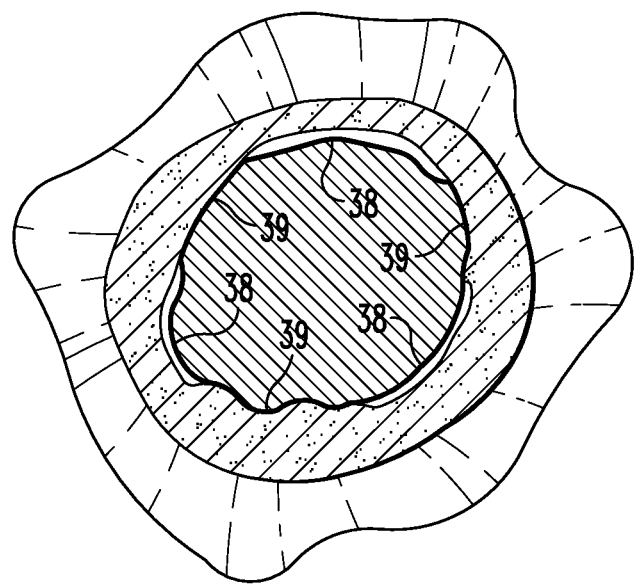
FIG. 9 is a cross-section of the gastroesophageal junction taken along the line 9-9 of FIG. 8 in the direction of the arrows showing a step in the process.

FIG. 9 shows a cross-section of esophagus adjacent to the lower esophageal sphincter. In order to accomplish the reduction in size of the gastroesophageal junction, multiple cuts 38 are accomplished circumferentially around the esophageal wall above the gastroesophageal junction while leaving untreated tissue 39 between each of the cuts as shown in FIG. 9. Although FIG. 9 shows three cuts 38 occurring above the gastroesophageal junction, it will be understood that any suitable number of cuts may be made in this region for reshaping purposes including 1 to 10 or more cuts, although 3 or 4 cuts will be more typical. Because the area below the gastroesophageal junction typically widens out, in instances where tissue is removed from both above and below the junction, a greater number of cuts and/or larger sized cuts will typically (but not necessarily) be made in this lower region compared to the relatively higher region. Nonetheless, regardless of whether tissue above the gastroesophageal junction is also being removed in a given procedure, any suitable number of cuts may be made in regions below the gastroesophageal junction for reshaping purposes including 1 to 10 or more cuts, although 3 or 4 cuts will be more typical. In one illustrative procedure as suggested by areas 40 and 41 in FIG. 8, a total of 7 cuts can be taken, with 3 above and 4 below the gastroesophageal junction. Although some treatment site locations have been described herein in relation to the gastroesophageal junction (GEJ, the most proximate part of gastric folds), it will be understood that treatment site locations useful in the present invention may also be described in relation to other anatomical markers or structures such as but not limited to the lower esophageal sphincter and the squamo-columnar junction (SCJ), also known as the Z-line. The SCJ (Z-line) is the endoscopically visible line formed by the juxtaposition of pale squamous epithelium and reddish columnar epithelium. In healthy individuals, this junction does not always precisely coincide with the GEJ, as it can also occur adjacent the GEJ, such as above the GEJ. The identification and use of these and other similar anatomical markers in the reshaping of body lumens will be well within the purview of skilled practitioners given the teachings herein.

In certain embodiments, the ligator barrel 25 is provided with calibrations inside of the barrel that are visible to the physician endoscopist, so that the amount of captured tissue 26 can be determined. In this manner, the endoscopist can estimate the size of the wound that will be produced at each treated site around the circumference of the lumen. In these and other embodiments, various forms of software may be utilized (whether incorporated directly into or otherwise used in conjunction with an inventive apparatus) to measure the diameter of the lumen and potentially address the size of the cuts necessary to provide the desired amount of reduction of lumen size.

Illustratively, the software can operate based upon one or more captured images including both the lumen region to be measured and at least one reference marker of known dimension positioned at the level of the lumen region to be measured. The image(s) can be imported into the software, and the user can generate an outline (e.g. circle) based on the reference marker, and an outline (e.g. circle) of the periphery of the lumen region to be measured. Using the known dimension of the reference marker, the software calculates the circumference of the lumen region on the basis of the relative dimensions of the outlines (e.g. circles). In some situations, the shape of the lumen will correspond precisely to the shape of the outline generated (e.g. circle). In these situations, multiple measurements can be taken, and a mean calculated based upon the multiple measurements, to serve as the circumference value for the procedure. As one example, to measure a size representative of the circumference of a gastroesophageal junction, an endoscope can be passed through the esophagus and into the stomach, and a retroflexed image can be captured of the endoscope shaft at the point where it enters the stomach (the "reference point"). This image can be imported into a software program as described above, and a first circle drawn to the outer dimension of the shaft at the reference point. A second circle can then be drawn to the inner periphery of the esophagus-stomach junction at the reference point. Using the known dimension of the first circle and a comparison to the second circle, the software calculates a value of the circumference of the second circle which serves as a representative value for the circumference of the junction. This process can be repeated multiple times if desired and a mean value calculated for the representative value. This representative value can then be used as a basis for deciding on a treatment regimen as described herein.

Since the healing process will take place after the cutting procedure so that the initial diameter of the treated portion of the esophagus will be somewhat larger than the expected final diameter, a software program can be beneficially used to guide the physician as to what percentage of the esophageal wall should be treated and/or what pattern of tissue removal utilized. As clinical experience is obtained, further correlations can be developed as to the amount and/or pattern of tissue removal required to produce a desired result. If the post-treatment gastroesophagel junction diameter reduction is not sufficient following healing, the endoscopist can perform one or more follow-up surgeries to make further resections to achieve the target diameter. On the other hand, if the junction area is made too small such that dysphagia becomes a problem, the procedure can be partially or completely reversed using standard esophageal dilation techniques (e.g., balloon dilatation) inasmuch as the muscle layer(s) below remains essentially intact. With the improved acid reflux barrier created by the inventive treatment, measurable pH should be improved above the gastroesophageal junction (a measure of treatment effectiveness).

Figure 10:
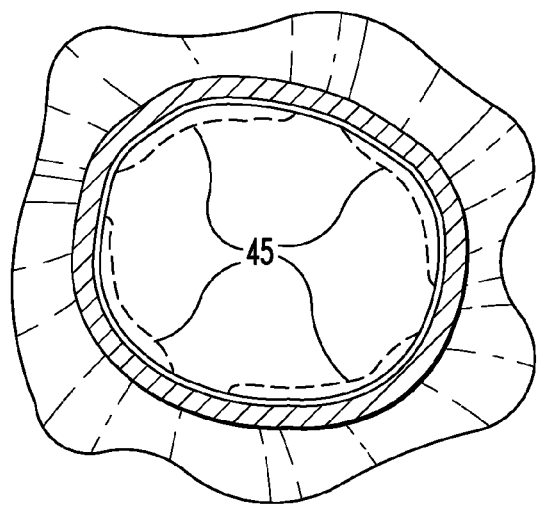
FIGS. 10-11 are cross-sectional views showing steps in an obesity treatment method.
Figure 11:
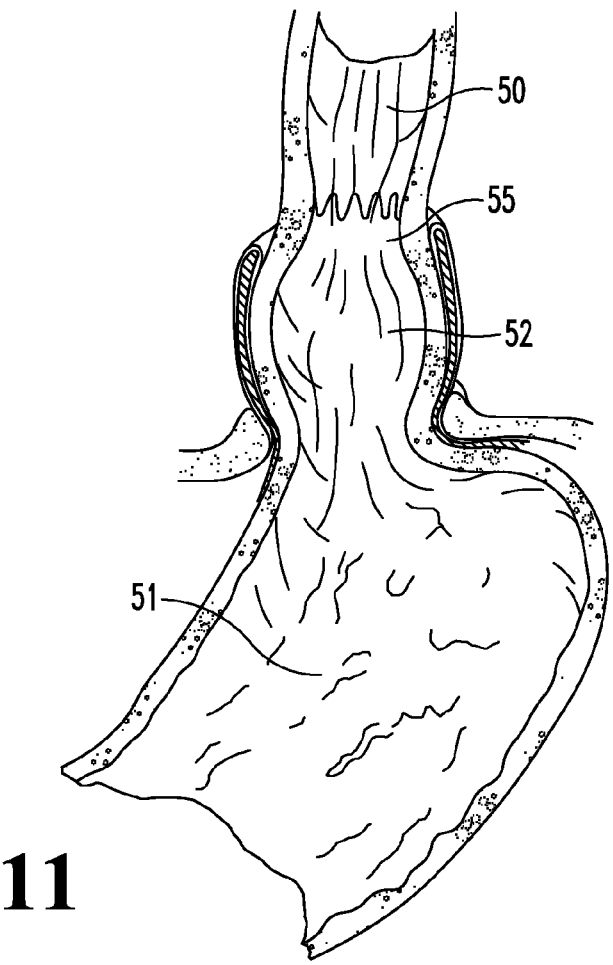

Methods of the invention may also be used in treating obesity. These methods can involve making a series of resections only below the gastroesophageal (GE) junction. As shown in FIG. 10, which is a cross-sectional view just below the GE junction (taken along line 10-10), the number of resections 45 may be four in number, although any suitable number of cuts may be made including 1 to 10 or more cuts, with 3 to 6 cuts being more typical. FIG. 11 shows the cross-section of the esophagus 50 and stomach 51 in which there is a hiatal hernia 52. In such a situation, fewer cuts at location 55 below the GE junction may be necessary. By narrowing the cardia below the GE junction, a smaller passageway for receiving food intake is established and, as a result, the patient will feel the sensation of satiety earlier. This will cause or assist the patient to stop eating earlier than he or she would otherwise do so. Of course, the patient may defeat the beneficial results of the procedure by eating small, more frequent meals; however, patient screening and counseling can be provided to patients undergoing bariatric treatment to increase the likelihood of a successful and long-term result.

Unlike the treatment for GERD, where in most cases no more than about 70-75% of the tissue defining the circumference of the inner surface of a body lumen wall is removed and/or traumatized, the obesity patient is expected to commonly benefit from removal of and/or damage to about 75% to about 100% of the tissue defining this body lumen wall inner surface, with higher amounts such as 90% to 100% sometimes being necessary to achieve the desired narrowing or other reshaping. In some embodiments, tissue is removed from 100% of the circumference of a body lumen wall at one or more longitudinal locations (e.g., 2 or 3) along the wall so as to provide one or more continuous "bands" of removed tissue along the wall. In many adult bariatric surgeries, a target lumen diameter of about 10 millimeters may be established. An advantage of more desired inventive procedures as compared to other bariatric surgeries is that they can be accomplished so as to be partially or completely reversible or otherwise adjustable. Thus, should the patient decide that he or she wants the procedure reversed or should reversal be necessitated for other reasons, standard dilatation techniques, e.g., using a dilatation balloon, can be undertaken.

Figure 12:
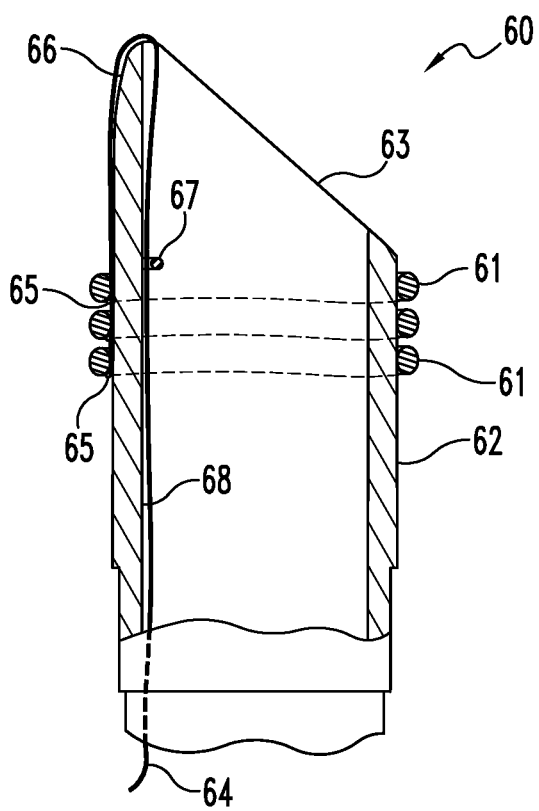
FIG. 12 provides a partial cross-sectional view of an illustrative beveled ligating barrel disposed upon the end of an endoscope.

In additional aspects of the invention, modified endoscopic ligator barrels and devices are provided. Referring to FIG. 12, such a device 60 may include multiple ligation bands 61 received upon a ligation barrel 62, potentially having a beveled barrel end 63, wherein the bands 61 are deployable by a single flexible pull line, such as string 64, extending through the barrel. In this regard, the pull string 64 can include a plurality of engagement members 65 configured to reside against and facilitate movement of the ligations bands 61 as the string 64 is pulled. The engagement members 65 can, for instance, be knots or polymeric beads positioned upon the string. The string 61 can then be situated in a looped pattern around the barrel 62 (see phantom lines illustrating loops) or linear or other pattern through the ligation bands in such a manner that pulling the string causes a controlled, sequential deployment of the bands. Illustrative pull string/ligation band looping arrangements that can be adapted as single-string configurations for use in aspects of the present invention are disclosed, for example, in U.S. Pat. Nos. 6,007,551, 6,730, 101 and 6,974,466, each of which is incorporated herein by reference.

In certain embodiments in which the barrel end 63 defines a bevel, the string will be positioned to exit the barrel 62 at or substantially at the long side 66 of the barrel so as to provide an enhanced deployment of the bands 61. As well, the ligation barrel 62 can include an internal or external adaptation to prevent migration of the string circumferentially around the barrel as it is pulled. Illustratively, an internal hoop or ring 67 can be attached to the inner barrel wall 68 and the string 64 passed therethrough to control the position of the string. Such single-string devices can be connected to the end of an endoscope and provide enhanced visibility through the barrel, while still allowing for effective band deployment. As well, it has been found that ligation bands received against the outer surface of a ligation barrel having a beveled tip can be successfully and effectively deployed employing longitudinallydirected pull string(s), despite the presence of the bevel. Accordingly, in one embodiment, a beveled-tip ligation barrel includes one or more tissue ligation bands positioned against its outer surface and one or more pull strings for deploying the band(s). Such barrels can be mounted to the end of an endoscope, and used for inventive reshaping methods as described herein or for other purposes.

In additional embodiments, the present invention provides kits for reshaping a body passage such as an esophagus or stomach, as described herein, that include means or devices as described herein for resecting or otherwise removing tissue from the lumen of the body passage, and written materials including instructions for use of the means or devices to reshape a body passage, e.g. in the treatment of GERD or obesity as described herein. The kits can include the means or devices packaged together with the instructions, e.g. in sterile medical packaging. Related embodiments of the invention include methods for distributing such means or devices, or otherwise conducting business, which include distributing such means or devices for reshaping a body passage, and also distributing information relating the use of such means or devices for reshaping a body passage. Such information can be distributed packaged with the means or device, or separately, e.g. including information or instructions available on a communication network, including a global computer communication network such as the internet.

For the purpose of promoting a further understanding of certain aspects of the present invention, the following Examples are provided. It will be understood that these Examples are illustrative, and not limiting, in nature.

EXAMPLE 1

Figure 13:
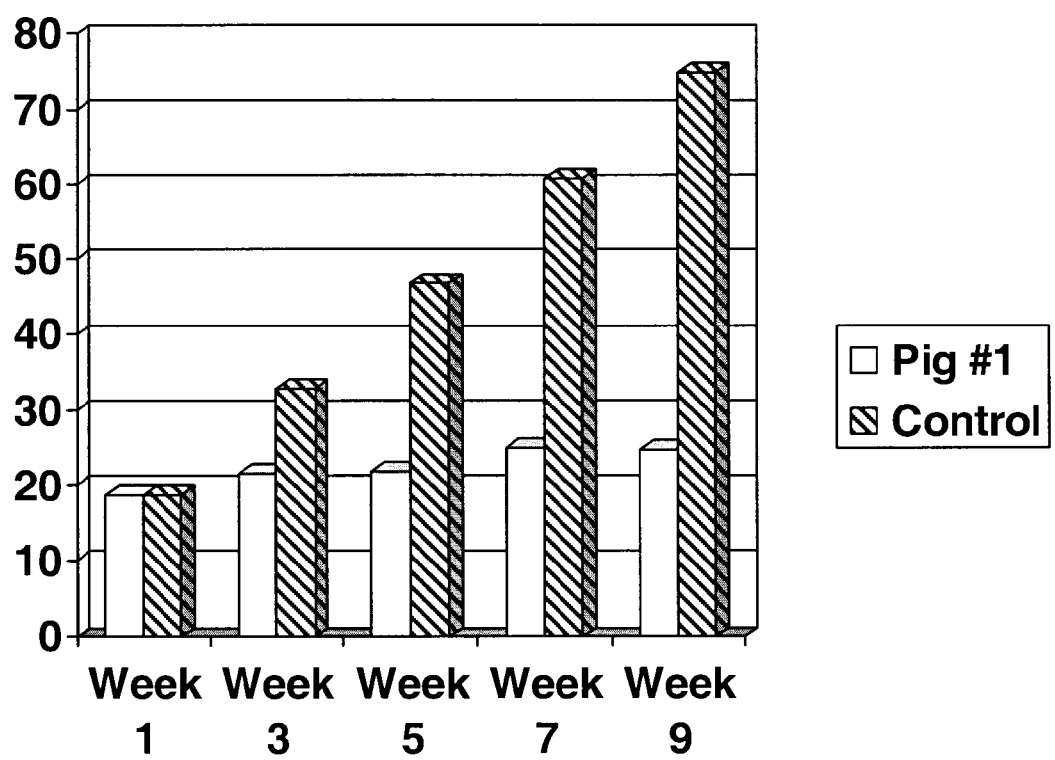
FIGS. 13-15 are graphs depicting results from an experimental study described in Example 1.
Figure 14:
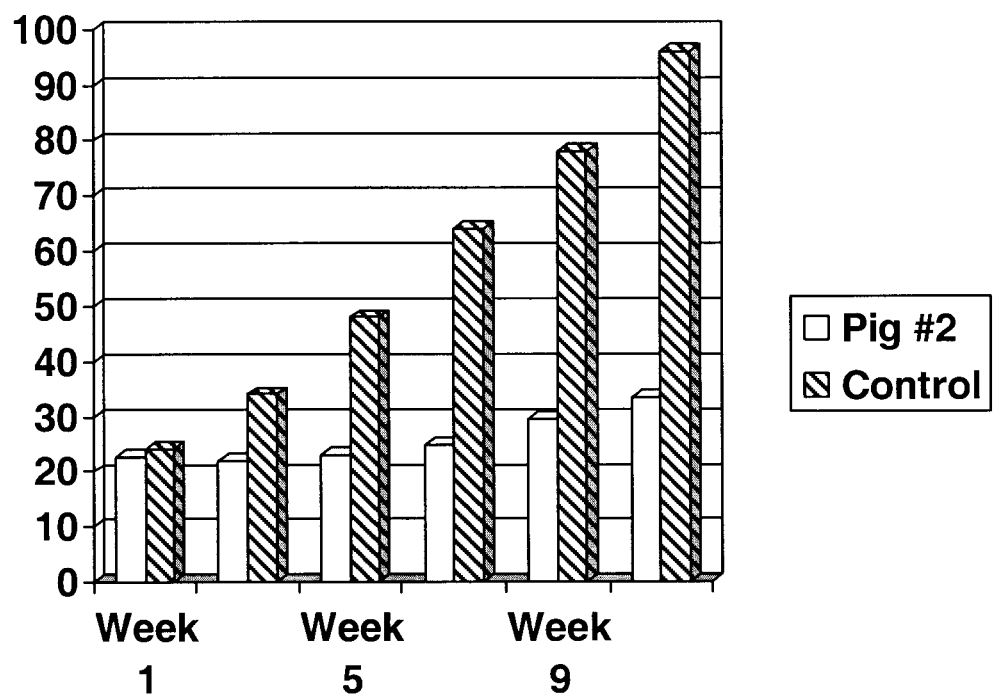
Figure 15:
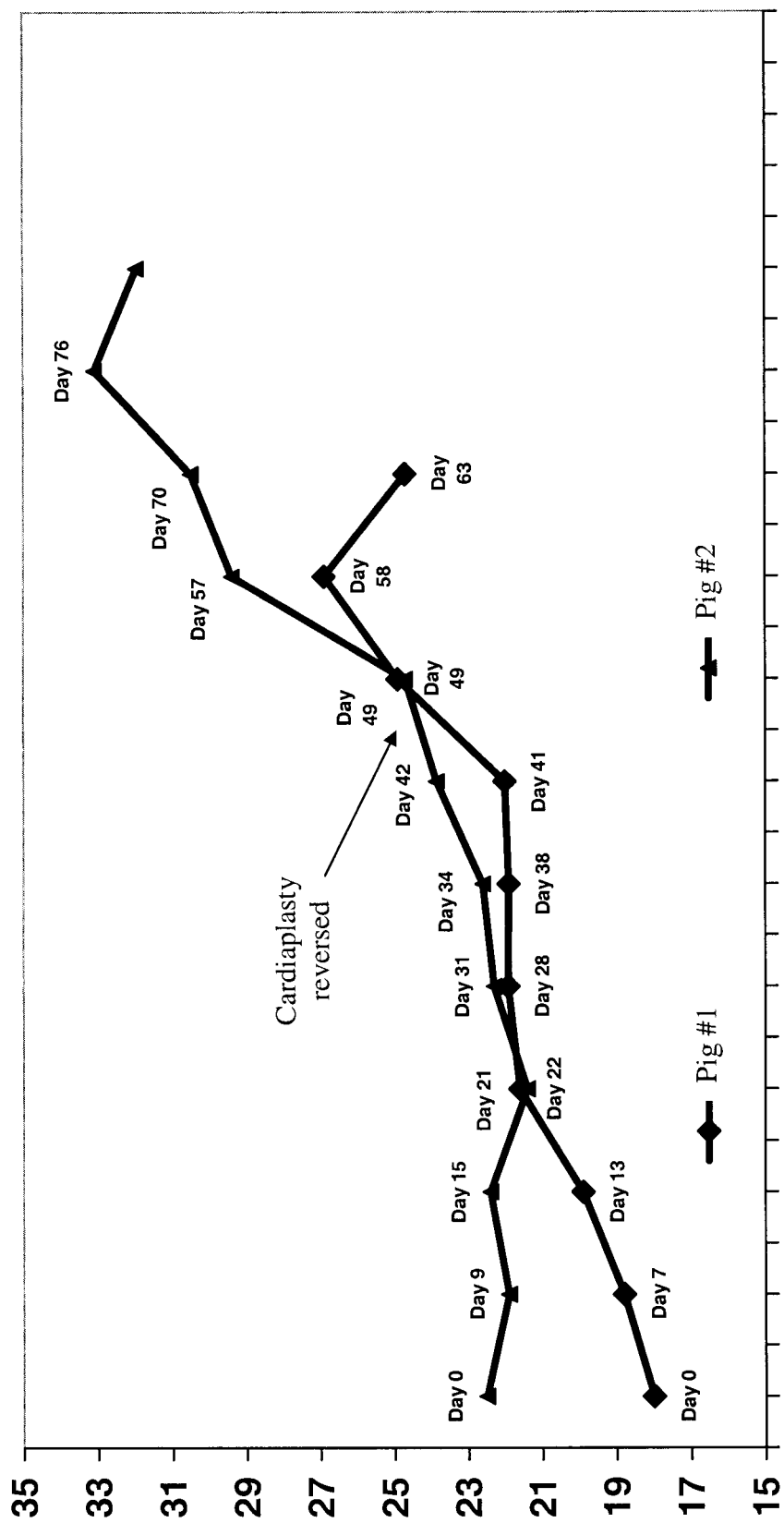

In this Example, endoscopic endoluminal mucoplasty (ELM) was performed on domestic farm pigs in a fashion that reshaped the gastroesophageal junction (GEJ) of the pigs. A first pig (Pig #1) underwent ELM of the cardia to reduce the diameter of the lumen at the (GEJ) by about one-half. To accomplish this, an endoscopic system equipped with the Duette® Multi-Band Mucosectomy device (Wilson-Cook Medical, Inc., dba Cook™ Endoscopy, Winston-Salem, N.C., USA) was used to band and resect tissue at 3 sites taken circumferentially around the cardia, representing about 70% of the circumference of the cardia. A second pig (Pig #2) was similarly treated, except the procedure was reversed after 5 weeks using a dilation balloon. These experimental pigs, along with controls, had access to an unlimited amount of food and full access to water. The pigs were healthy and active throughout the study. The results of the study are presented graphically in FIGS. 13, 14 and 15. As can be seen, the treated pigs experienced significantly less weight gain (shown in pounds) than the controls. Additionally, Pig #2 experienced accelerated weight gain following reversal of the procedure.

EXAMPLE 2

In this Example, endoscopic endoluminal mucoplasty (ELM) was used to perform a fundoplasty on a domestic farm pig. An endoscopic system was used, equipped with the Duette® Multi-Band Mucosectomy device as in Example 1. Repeated banding and resection was used to remove 10 square centimeters of the mucosa and submucosa of the fundus of the stomach. The fundus, which is the most expansible part of the stomach, was shrunken and reshaped upon healing after the resection. This pig along with a control had access to an unlimited amount of food and full access to water over five weeks. The pigs were healthy and active throughout the study, and the treated pig experienced significantly less weight gain than the control pig.

While the illustrated embodiments have been detailed in the drawings and foregoing description, the same is to be considered as illustrative and not restrictive in character, it being understood that only the preferred embodiment has been shown and described and that all changes and modifications that come within the spirit of the invention are desired to be protected. The articles "a", "an", "said" and "the" are not limited to a singular element, and include one or more such elements.

What is claimed is:

1. A medical device, comprising:
an endoscopic ligator barrel having a distal end;
a plurality of ligation bands received upon the ligator barrel;
a single pull line operably associated with the plurality of ligation bands, the single pull line extending distally through the ligator barrel and exiting the barrel from the distal end to bend over the distal end of the barrel and extend proximally towards the plurality of ligation bands, wherein a portion of the single pull line is situated outside the ligator barrel, and wherein the single pull line extends only once over the distal end of the barrel and is operable to deploy the plurality of ligation bands from the ligator barrel; and
a guide member projecting from a surface of the ligator barrel proximal to the distal end, wherein the guide member surrounds the single pull line, and wherein the single pull line passes through the ligator barrel and the guide member before engaging the plurality of ligation bands;
wherein the ligator barrel includes a first side that is generally opposite a second side, the first side extending distally of the second side in a generally longitudinal direction along the ligator barrel; and
wherein the single pull line exits the barrel at or substantially at the first side of the barrel and is retained at or substantially at the first side by the guide member as the plurality of ligation bands are deployed from the ligator barrel by the single pull line.

2. The medical device of claim 1 further comprising an endoscope, with the endoscopic ligator barrel received upon the endoscope.

3. The medical device of claim 1, wherein the ligator barrel includes a distal end bevel located between the first side and the second side.

4. The medical device of claim 3, wherein the ligator barrel has a width and the distal end bevel extends substantially across that width.

5. The medical device of claim 1, wherein the ligator barrel is provided with calibrations for determining an amount of tissue received in the ligator barrel.

6. The medical device of claim 1, wherein the plurality of ligation bands are positioned along a longitudinal segment of the endoscopic ligator barrel, and wherein the circumference of the barrel is substantially constant along the length of the longitudinal segment.

7. The medical device of claim 1, wherein the guide member projects from a location proximal to the second side of the distal end.

8. A medical device, comprising:
an endoscopic ligator barrel having a proximal end and a beveled distal end with the beveled distal end including a bevel that travels generally from a first side of the ligator barrel to an opposite and comparatively shorter second side of the ligator barrel;

a plurality of ligation bands received upon the ligator barrel, the plurality of ligation bands being deployable from the beveled distal end;

a single pull line extending through the endoscopic ligator barrel and exiting the ligator barrel from the beveled distal end, the single pull line bending over the beveled distal end only once and being operably associated with the plurality of ligation bands for deploying the plurality of ligation bands from the ligator barrel; and a guide member defining a guide lumen projecting transverse to a surface of the ligator barrel, the guide lumen encompassing the single pull line, wherein the single pull line passes through the ligator barrel and the guide lumen;

wherein the first and second sides of the ligator barrel each have an inner barrel wall surface and an outer barrel wall surface;

wherein the single pull line exits the ligator barrel at an exit location at or substantially at the first side of the ligator barrel, the guide member configured to prevent circumferential migration of the exit location around the ligator barrel as the single pull line is pulled to deploy the plurality of ligation bands; and wherein a first portion of the single pull line extends from the guide member to the exit location before engaging the plurality of ligation bands, and a second portion of the single pull line extends proximally from the guide member.

9. The medical device of claim 8, wherein the endoscopic ligator barrel has a width and the bevel travels across that width in a general first direction.

10. The medical device of claim 8, wherein the plurality of ligation bands are positioned along a longitudinal segment of the endoscopic ligator barrel, and wherein the circumference of the barrel is substantially constant along the length of the longitudinal segment.

11. The medical device of claim 8, wherein the single pull line comprises a plurality of engagement members configured to reside against and facilitate movement of the plurality of ligation bands as the single pull line is pulled.

12. A medical device, comprising:
an endoscopic ligator barrel;
a plurality of ligation bands received upon the ligator barrel and deployable from a distal end of the ligator barrel;
a single pull line extending through the endoscopic ligator barrel and over the distal end and being operably associated with the plurality of ligation bands for deploying the plurality of ligation bands from the ligator barrel, wherein the ligator barrel includes a first side and a second side, the first side extending distally of the second side at the distal end of the ligator barrel; and
a guide member positioned on an inside surface of the ligator barrel proximal to the distal end, wherein the guide member defines a guide lumen encircling the single pull line, and wherein the single pull line passes through the ligator barrel and the guide lumen before engaging the plurality of ligation bands;
wherein the single pull line exits the ligator barrel at an exit location and bends over the distal end only once, the exit location being at or substantially at the first side of the ligator barrel; and
wherein the single pull line is retained at the exit location by the guide member as the plurality of ligation bands are deployed from the ligator barrel by the single pull line.

13. The medical device of claim 12, wherein the distal end of the ligator barrel is beveled.

14. The medical device of claim 12, wherein the ligator barrel has a width and includes a distal end bevel that travels substantially across that width between the first side and the second side.

15. The medical device of claim 12, wherein the guide member is configured to prevent circumferential migration of the single pull line as the plurality of ligation bands are deployed.

16. The medical device of claim 12, wherein the guide member is proximal to the second side of the distal end.

17. A medical device, comprising:
an endoscopic ligator barrel having a beveled distal end including a first side that is generally opposite a second side;
a ligation band received upon the ligator barrel and situated at a first location in which the ligation band is proximal of the distal end and extends in a generally transverse direction relative to the longitudinal axis of the ligator barrel, wherein the distance between the ligation band and the distal end of the ligator barrel along the first side of the barrel is greater than the distance between the ligation band and the distal end of the ligator barrel along the second side of the barrel when the ligation band is situated at the first location;
a single pull line extending through the endoscopic ligator barrel and being operably associated with the ligation band for deploying the ligation band from the ligator barrel with the single pull line exiting the ligator barrel at or substantially at the first side of the ligator barrel and bending over the beveled distal end before extending towards the ligation band; and
a guide member included on an inside or outside surface of the endoscopic ligator barrel proximal to the distal end at the first side, the guide member configured to surround the pull line retaining the pull line at or substantially at the first side as the ligation band is deployed from the ligator barrel by the single pull line;
wherein the single pull line bends over the beveled distal end only once.

18. The medical device of claim 17, wherein the guide member defines a guide lumen, and wherein the single pull line passes through the guide lumen before exiting the ligator barrel.

19. The medical device of claim 17, wherein the ligator barrel is provided with calibrations for determining an amount of tissue received in the ligator barrel.

20. The medical device of claim 17, wherein the guide member is configured to prevent circumferential migration of the single pull line as the ligation band is deployed.

21. The medical device of claim 17, wherein the ligation band is positioned along a longitudinal segment of the endoscopic ligator barrel, and wherein the circumference of the barrel is substantially constant along the length of the longitudinal segment.

22. The medical device of claim 17, wherein the guide member is proximal to the second side of the distal end.

* * * * *